United States Patent [19]
Booth, Jr. et al.

[11] Patent Number: 5,540,696
[45] Date of Patent: Jul. 30, 1996

[54] INSTRUMENTATION FOR USE IN ORTHOPAEDIC SURGERY

[75] Inventors: Robert E. Booth, Jr., Philadelphia, Pa.; Gregory C. Stalcup, Columbia City, Ind.; Rodney Bays, Pierceton, Ind.; Billy N. Sisk, Claypool, Ind.; Timothy R. Miller, Warsaw, Ind.

[73] Assignee: Zimmer, Inc., Warsaw, Ind.

[21] Appl. No.: 369,226

[22] Filed: Jan. 6, 1995

[51] Int. Cl.$^6$ .......................... A61B 17/15; A61B 17/66
[52] U.S. Cl. .......................... 606/88; 606/90; 606/102; 606/105
[58] Field of Search .................. 606/102, 105, 606/96, 97, 98, 90, 86, 87, 88; 254/95, 96, 97

[56] References Cited

U.S. PATENT DOCUMENTS

| | | | |
|---|---|---|---|
| 692,536 | 2/1902 | McDermid | 254/95 |
| 4,501,266 | 2/1985 | McDaniel . | |
| 4,566,448 | 1/1986 | Rohr, Jr. . | |
| 4,567,886 | 2/1986 | Petersen . | |
| 4,574,794 | 3/1986 | Cooke et al. . | |
| 4,655,197 | 4/1987 | Atkinson . | |
| 4,703,751 | 11/1987 | Pohl . | |
| 4,907,578 | 3/1990 | Petersen | 606/79 |
| 4,938,762 | 7/1990 | Wehrli | 606/88 |
| 5,116,338 | 5/1992 | Poggie et al. | 606/90 |
| 5,213,112 | 5/1993 | Niwa et al. | 128/774 |
| 5,282,803 | 2/1994 | Lackey | 606/80 |
| 5,342,367 | 8/1994 | Ferrante et al. | 606/86 |
| 5,342,368 | 8/1994 | Petersen | 606/88 |
| 5,344,423 | 9/1994 | Dietz et al. | 606/87 |
| 5,364,401 | 11/1994 | Ferrante et al. | 606/84 |
| 5,417,695 | 5/1995 | Axelson, Jr. | 606/89 |
| 5,454,816 | 10/1995 | Ashby | 606/88 |

OTHER PUBLICATIONS

AOR Knee Instrumentation, Thomas Petersen, M.D., Jo Miller, M.D., Jorge O. Galante, M.D., (Zimmer, Inc.).
New Jersey LCS Total Knee System, Frederick K. Buechel, M.D. (DePuy).

*Primary Examiner*—Gary Jackson
*Assistant Examiner*—Scott Markow
*Attorney, Agent, or Firm*—Todd A. Dawson

[57] ABSTRACT

The instrumentation set of this invention assists the surgeon in selecting the proper implant components, in determining the amount of distal bone to resect, and in aligning instrumentation designed to resect the bone. The instrumentation set provides numerous systems for verifying to the surgeon that he has correctly aligned the instruments prior to removing any bone.

The set includes a rotational alignment guide, which aids the surgeon in establishing the appropriate rotational alignment for the knee as determined by reference to standard femoral landmarks such as the posterior condyles and epicondyles. The rotational alignment guide includes a slot for guiding a saw blade for removal of the posterior condyles of the femur.

The set further includes a tensor designed to tense the knee joint in flexion and extension. The tensor is activated by a torque wrench so that a measured amount of tension force can be applied to the joint. The tensor is configured to slidably carry sizing rods, which contact the femur and include a plurality of markings, which relate to the size of the femur as well as the spacing between the femur and tibia. This information is used by the surgeon to select the proper size of femoral and tibial articulate surface components. The sizing rods are connected to the tensor when the tibial is in flexion and in extension, which will indicate to the surgeon any variation required in the amount of bone to be resected.

12 Claims, 16 Drawing Sheets

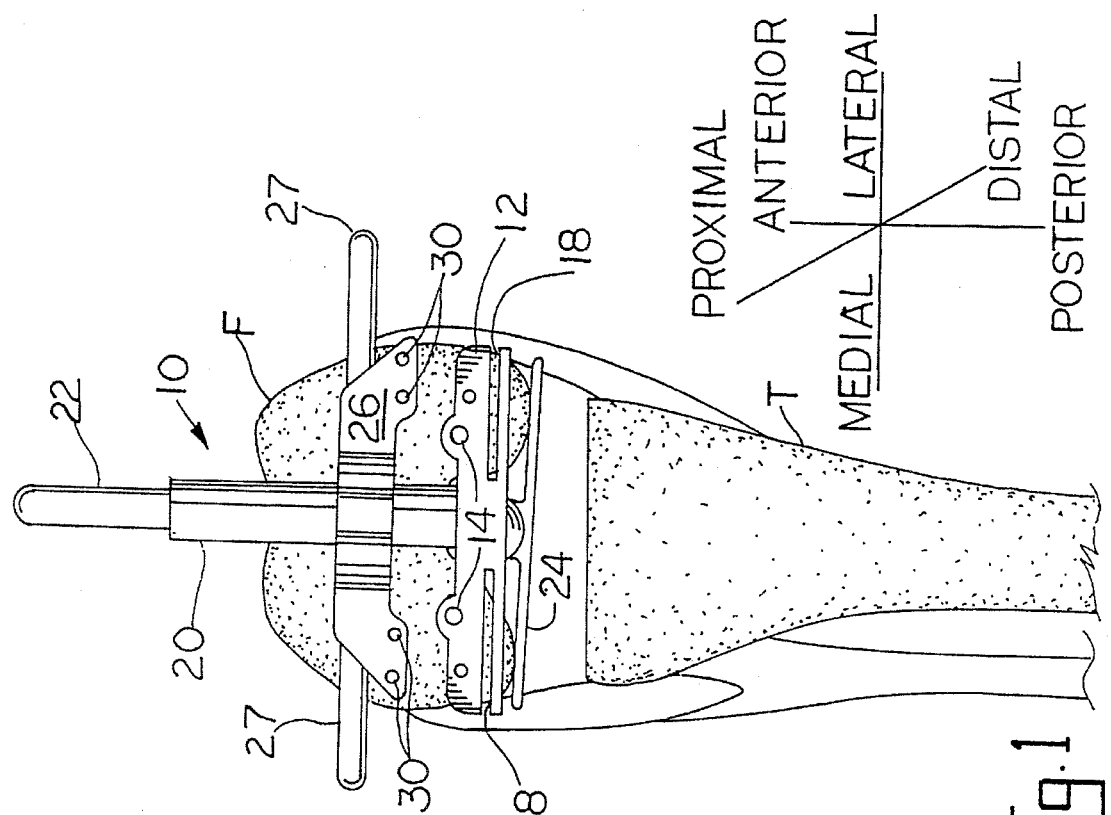
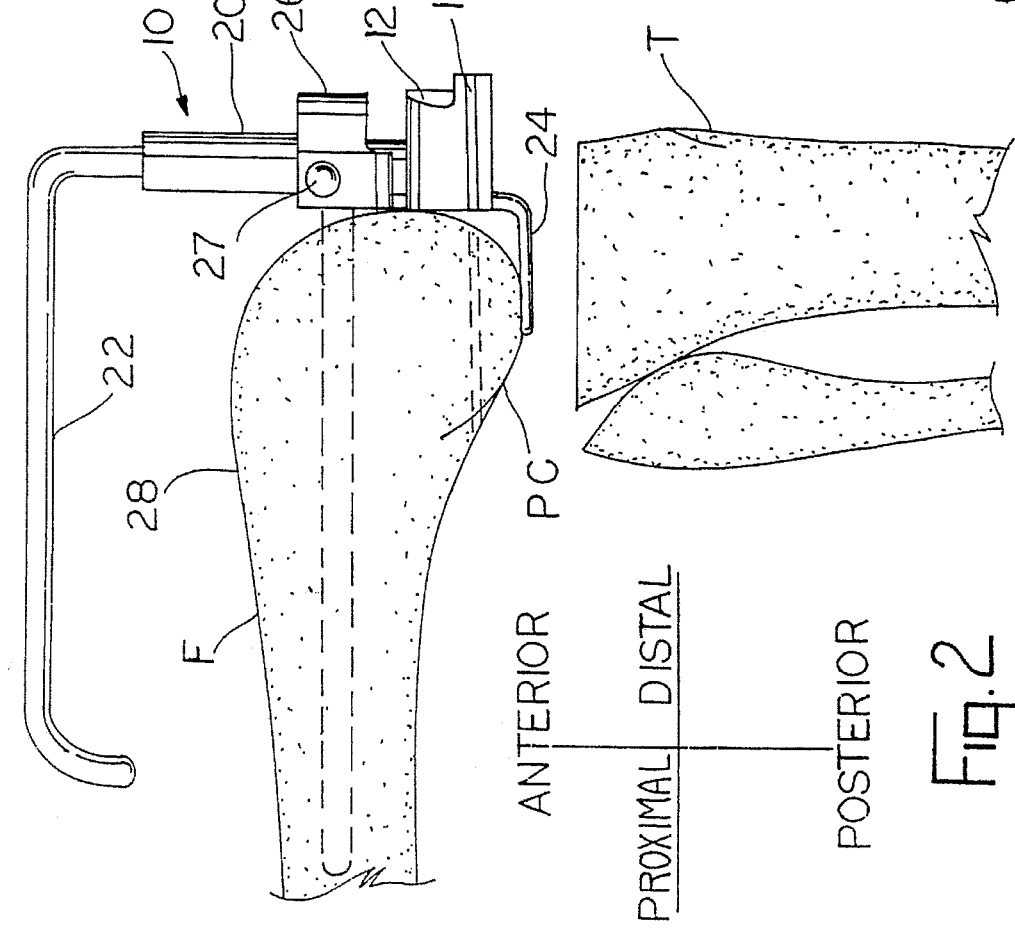

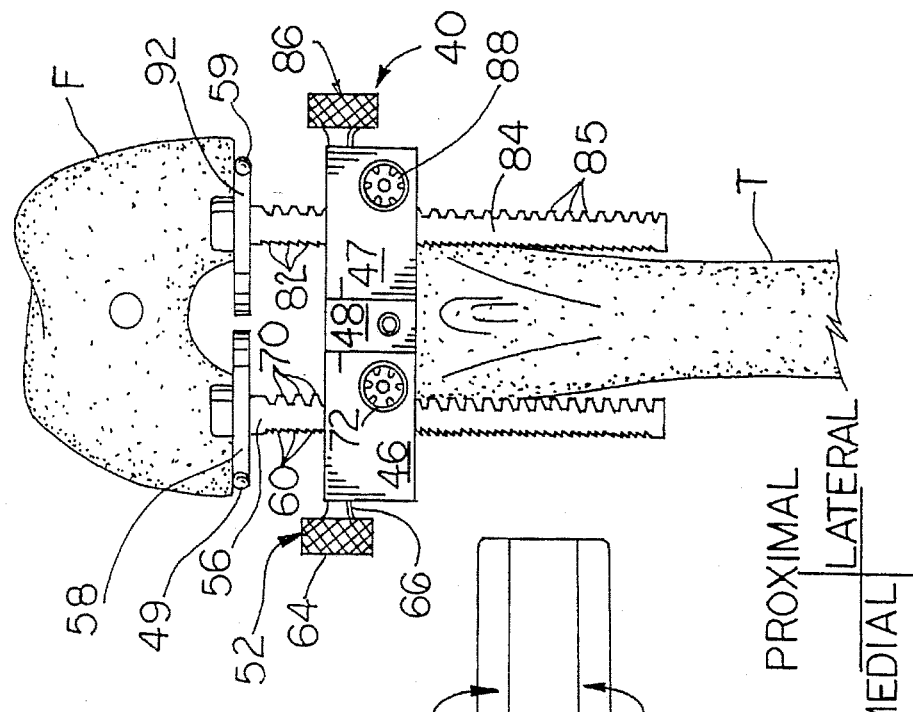
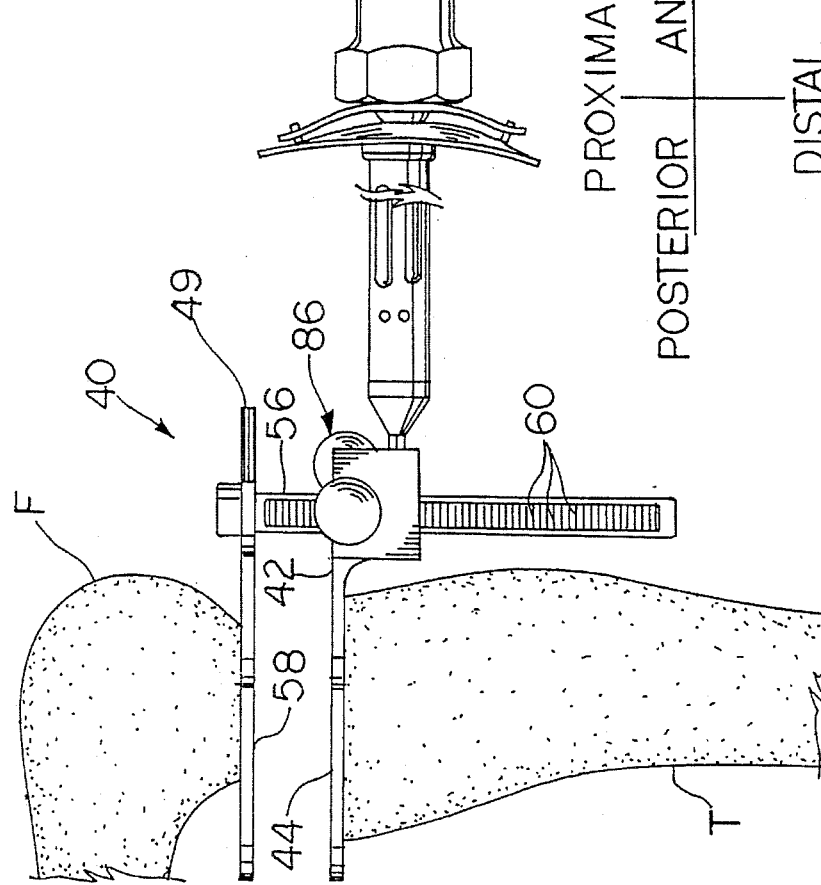

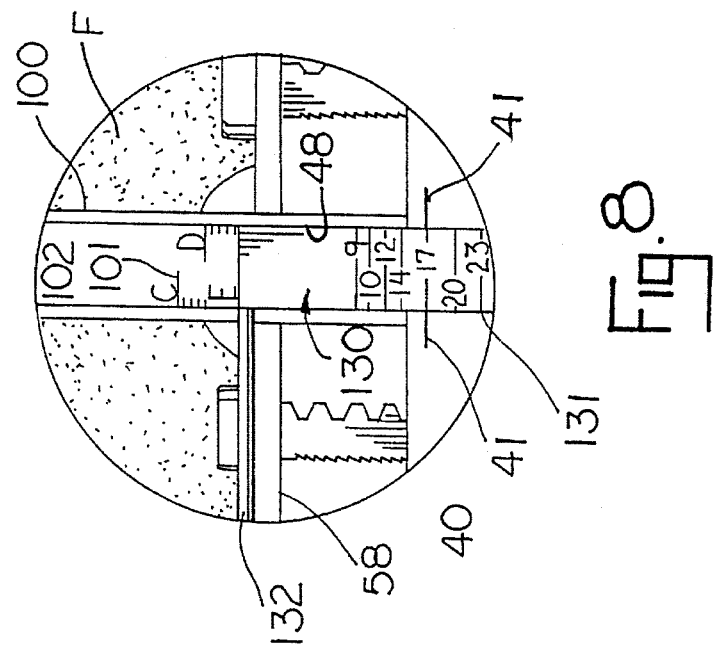
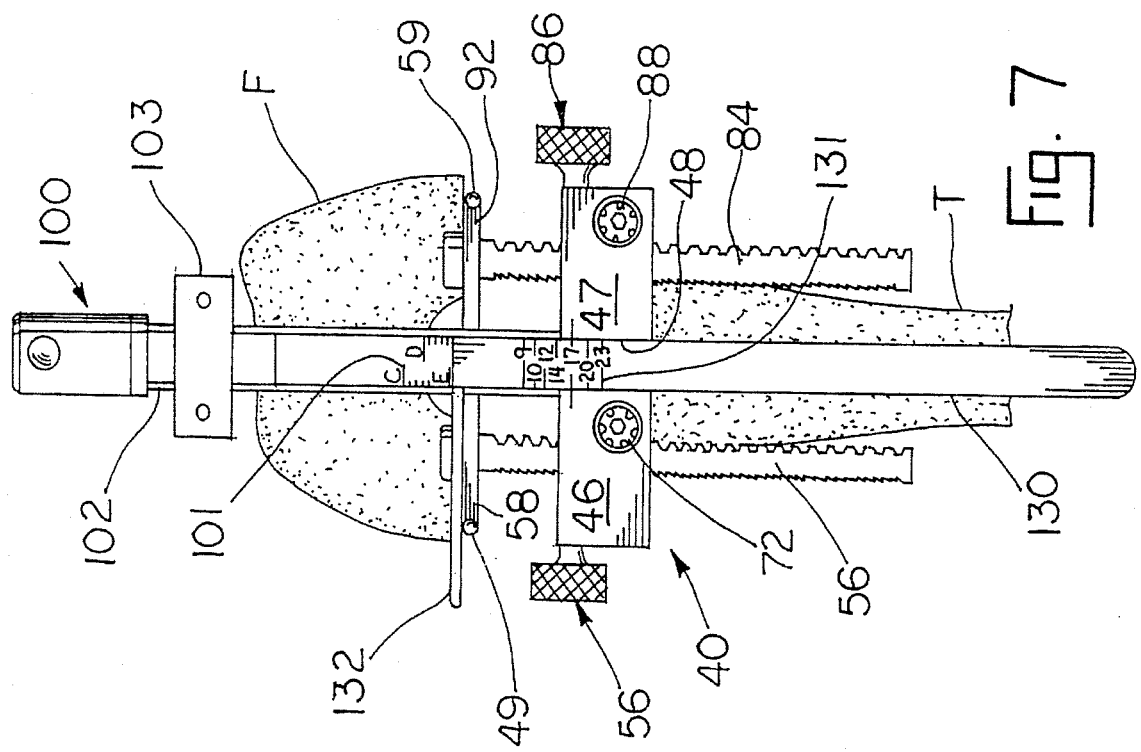

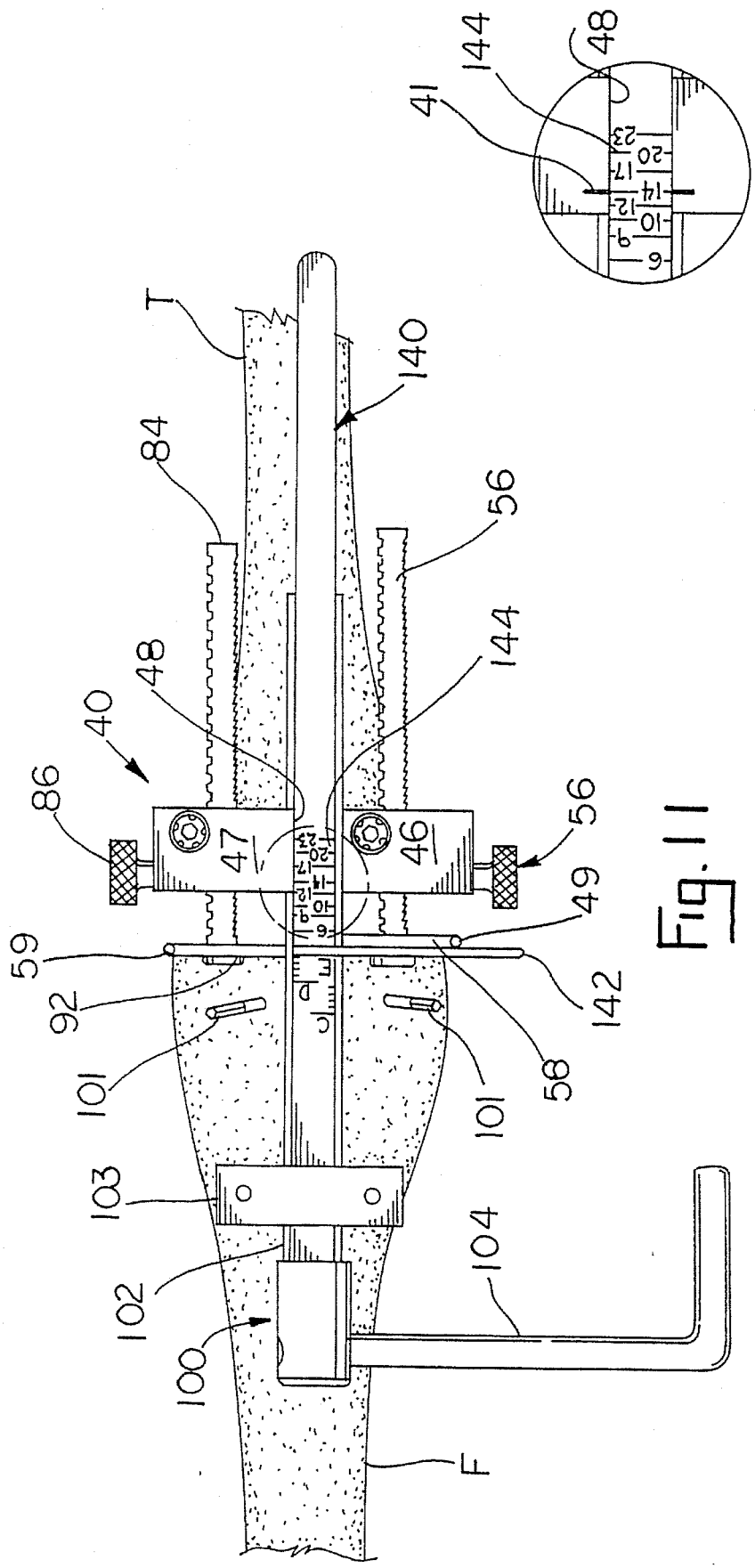

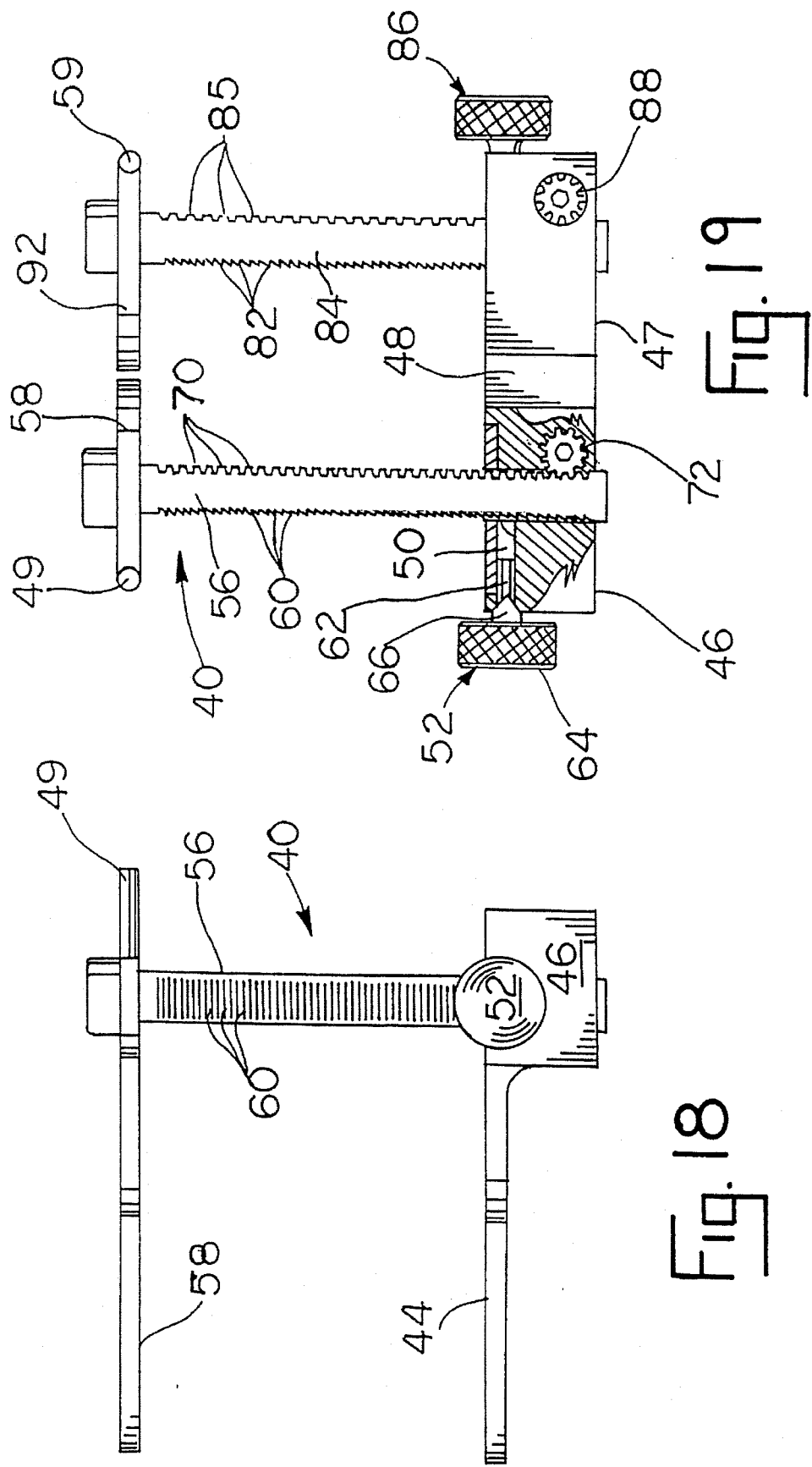

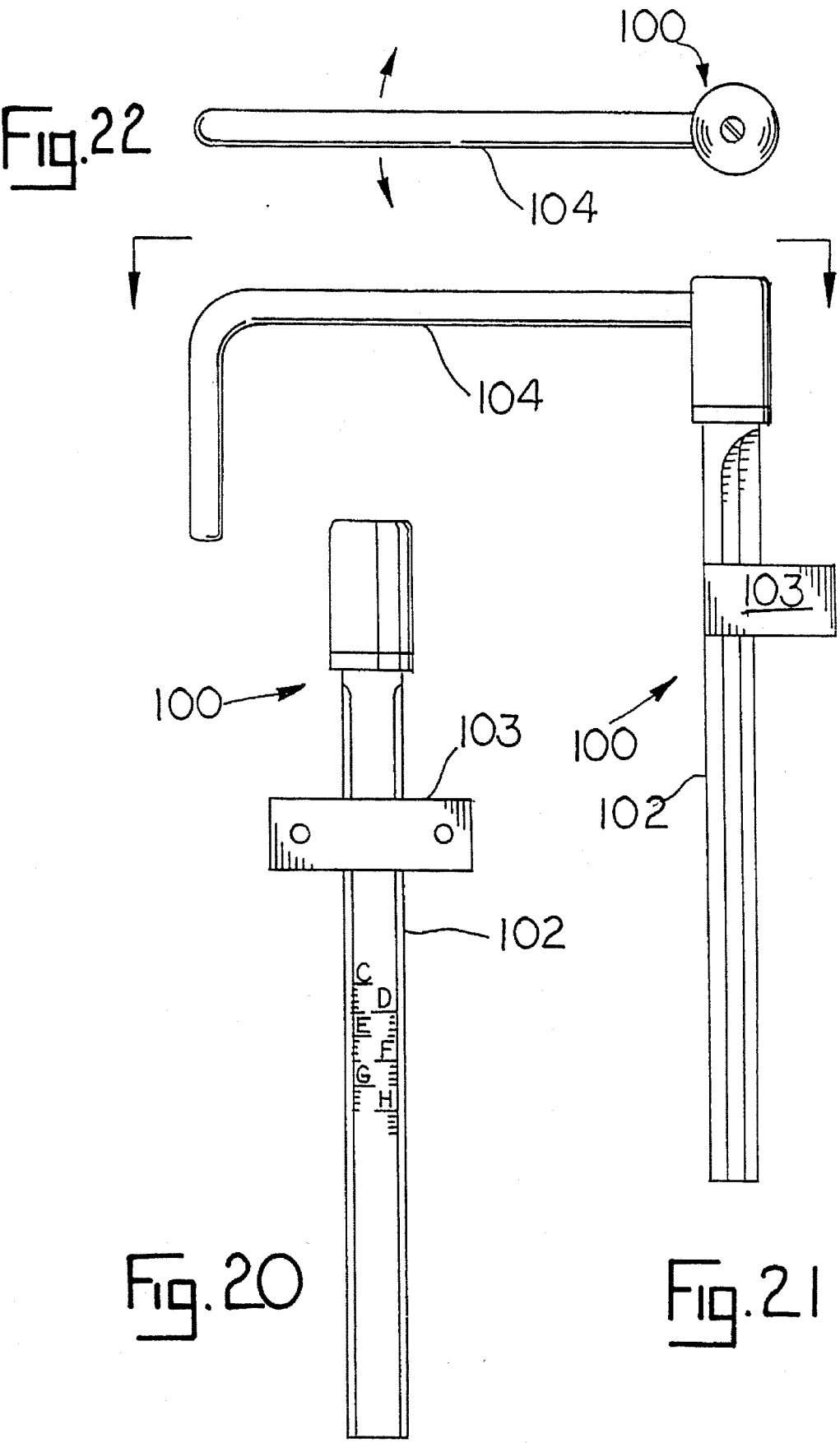

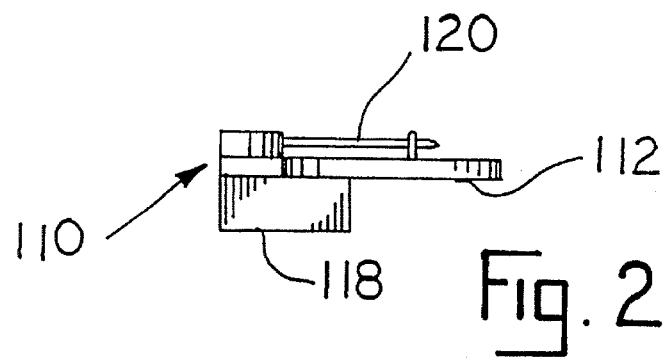
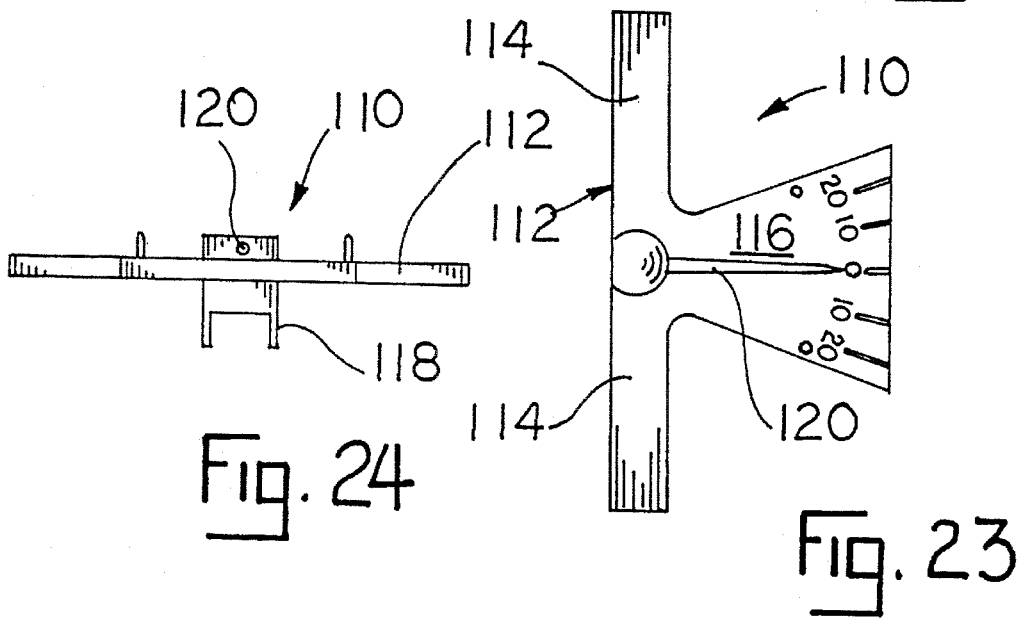

INSTRUMENTATION FOR USE IN ORTHOPAEDIC SURGERY

FIELD OF THE INVENTION

This invention relates to instrumentation used in orthopaedic surgery during a total knee replacement procedure for sizing the femur and polyethylene components as well as providing indications of proper alignment and assisting the surgeon in providing the proper soft tissue balance for the joint.

BACKGROUND OF THE INVENTION

In a total knee arthroplasty procedure to replace a worn or damaged knee, the orthopaedic surgeon spends a good deal of time ensuring the resulting knee joint will be balanced. A balanced knee joint will demonstrate proper ligament tension through the joint's range of motion as well as a predetermined angle between the mechanical axis of the knee and the anatomical axis of the knee. This provides for a more natural acting joint prosthesis and improves the wear characteristics of the prosthesis. Selecting the proper size of prosthetic components is also an important factor which affects the success of the procedure. If the wrong components are selected, the tendons could be too tight or too loose resulting in poor performance for the knee.

SUMMARY OF THE INVENTION

The instrumentation set of this invention assists the surgeon in selecting the proper size of implant components, in determining the amount of distal bone to resect, in providing the proper soft tissue balance, and in aligning instrumentation designed to resect the bone. The instrumentation set provides for numerous systems for verifying to the surgeon that he has correctly aligned the instruments and balanced the joint prior to resecting the femur.

The set includes a rotational alignment guide, which aids the surgeon in establishing the appropriate rotational alignment for the knee as determined by reference to standard femoral landmarks such as the posterior condyles and epicondyles. The rotational alignment guide includes a slot for guiding a saw blade for removal of the posterior condyles of the femur.

The set further includes a tensor designed to tense the knee joint in flexion and extension. The tensor is activated by a torque wrench so that a measured amount of tension force can be applied to the joint. The tensor is configured to slidably carry sizing rods which contact the femur and include a plurality of markings relating to the size of the femur as well as the spacing between the femur and tibia. This information is used by the surgeon to select the proper size of femoral and tibial articulate surface components. The sizing rods are connected to the tensor when the knee joint is in flexion and in extension which will indicate to the surgeon any variation required in the amount of bone to be resected.

Accordingly, it is an advantage of this invention to provide for a novel set of instruments for tensioning and sizing the knee joint.

Another advantage of the invention is to provide a novel tensioning device wherein the knee joint may be placed in tension in a flexed and/or extended position.

Another advantage of the invention is to provide a novel system for measuring the knee joint, including instruments for measuring the gap between the tibia and femur as well as measuring the size of the femur.

Yet another advantage of the invention is to provide for a set of instruments that determine the amount of bone to be resected relative to a standard resection.

Still other advantages of the invention will become apparent upon a reading of the following description taken with the accompanying drawings.

BRIEF DESCRIPTION OF THE DRAWINGS

FIGS. 1 through 13 illustrate the progression of the set of instruments of the invention and their mode of operation during a knee replacement surgery.

FIG. 18 is a side elevational view of the tensor of the invention.

FIG. 19 is an end view of the tensor of FIG. 18.

FIG. 20 is an elevational view of the femoral sizer and drill guide of the invention.

FIG. 21 is a side elevational view of the invention of FIG. 20.

FIG. 22 is an end elevational view of the invention of FIG. 21.

FIG. 23 is an elevational view of the angle indicator of the invention.

FIG. 24 is an end elevational view of the invention of FIG. 23.

FIG. 25 is a side elevational view of the invention of FIG. 23.

DESCRIPTION OF THE PREFERRED EMBODIMENT

Figure 6:
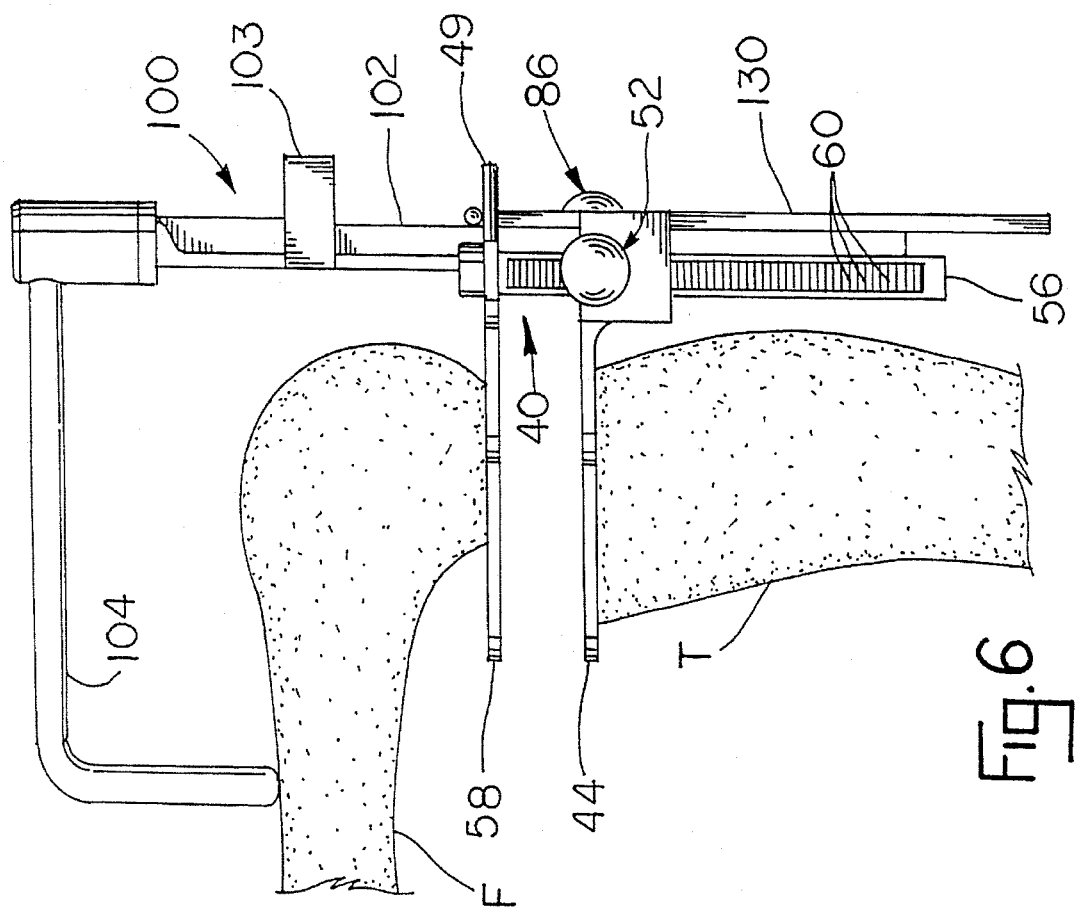

The preferred embodiment herein described is not intended to be exhaustive or to limit the invention to the precise form disclosed. Rather, it is chosen and described to best explain the invention so that others skilled in the art might utilize its teachings.

FIGS. 1 through 13 illustrate the individual instruments of the instrument set as they would be used in surgery. The figures are arranged in a manner such that the instruments are presented in the order that they would be used in an actual knee replacement surgery. The description of the invention will therefore begin with a general description of the use of the instruments as illustrated in FIGS. 1–13. A more specific description of each of the instruments will follow.

To provide the reader with the proper orientation of the instruments and to assist in more fully understanding the construction of the instruments, a small chart is included on many of the figures. The charts indicate the general directions—anterior, posterior, medial, and lateral, as well as proximal and distal. These terms relate to the orientation of the femur and will be used in the descriptions of the various instruments consistent with their known medical usage.

Preoperatively, the surgeon obtains a number of x-rays of the patient's leg. The surgeon uses the x-rays to determine the angle between the anatomical and mechanical axes of the joint. The surgeon may also determine the angle between the transverse axis and the plain formed by the distal femoral condyles.

During surgery the knee joint is exposed and the proximal end of the tibial (T) is resected to form a flattened tibial plateau which is substantially perpendicular to the mechanical axis of the joint. The resection can be achieved by a standard saw blade and guide or by milling. A device for milling the distal tibial surface is illustrated in U.S. Pat. No. 5,344,423. The surgeon then forms an opening into the intramedullary canal of the femur (F) in a known manner.

The surgeon must now establish the rotational alignment of the femur. To do so, the intramedullary rod 6 of the rotational alignment guide 10 is inserted into the femur as illustrated in FIGS. 1 and 2. The guide 10 is inserted until the body 18 of the guide contacts the distal femur. During insertion of the guide, the surgeon manually adjusts the position of the guide body 10 relative to the femur so that the reference feet 24 contact the posterior condyles (PC) as illustrated in FIG. 1. The angle between the reference feet and the body 18 may either be fixed or may be adjustable to provide for the proper rotational alignment of the knee. If the angle of the reference feet is fixed, a set of feet would be supplied with the instrument, each being set at a predetermined angular alignment. With the instrument properly positioned as illustrated in FIG. 1, the posterior surface of the body should be parallel to the tibial plateau. This provides a quick visual indication to the surgeon of proper alignment of the instrument. To further verify the proper alignment, the surgeon may visually align the rotational alignment guide with known anatomical landmarks such as the posterior condyles, the epicondyles or the anterior femur. Once the surgeon is satisfied with the alignment of the alignment guide 10, a pin is inserted into at least one throughbore 30 of pinning guide 26 on either side of tube 20 to make a mark in the femur for later use. Similarly, the body is pinned to the distal femur. The posterior condyles are removed with a saw blade (not shown) as guided by the guide slots in the body of the rotational alignment guide 10. The rotational alignment guide is then removed.

Next the surgeon places the flexed knee joint in tension by inserting the tensioner 40 between the tibia and femur as illustrated in FIG. 3. The tensioner includes a first paddle 44 which contacts the resected proximal tibia and a second set of paddles 58, 92 which contact the resected posterior femoral condyles as illustrated in FIGS. 3 and 4. The second set of paddles are connected to independent ratchet drives 72, 88 which extend the distance between the paddles 58, 92, and 44. A torque driver (TD) is used to spread the second set of paddles from the first paddle until a predetermined amount of force is exerted between the femur and the tibia. The tensioner includes ratchet pawls for preventing the second set of paddles from inadvertently shifting toward the first paddle. Tensing the flexed knee joint allows the surgeon to balance and fine tune the soft tissue. Balancing the soft tissue is accomplished in a variety of known methods such as placing a small incision into one of the ligaments to allow the ligaments to "release" or stretch a small amount. If the soft tissue balance requires a more significant adjustment, the surgeon can opt to readjust the instruments of the invention or may choose to recut the tibia.

Figure 5:
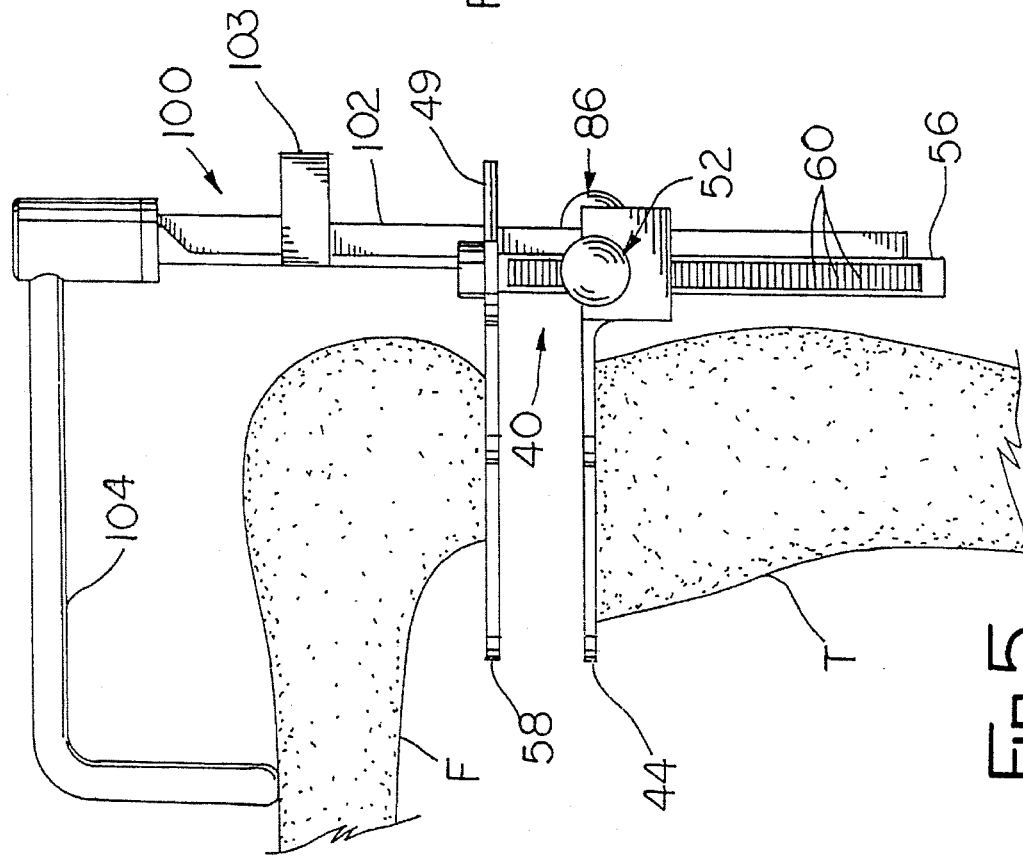

With the knee flexed and tensed, (FIGS. 3 and 4) the femoral sizer 100 is slid into the T shape slot 48 of tensor 40 until the sizer arm 104 contacts the anterior surface of the femur (FIGS. 5 and 6). Next the surgeon slides the flexion poly thickness guide 130 onto the tensor in an overlying relationship to the femoral sizer within slot 48 of tensor 40 (FIG. 7). The flexion poly thickness guide includes a transverse arm 132 which contacts a rod 49 of a tensor paddle 58 as illustrated in FIG. 7. The sizer guide 100 includes a plurality of indicia 101 thereon relating to the size of the femoral component required for the femur. The flexion poly thickness guide 130 includes a plurality of indicia 131, which relates to the thickness of the poly component required in flexion as well as indirectly indicating the amount of distal femoral bone to be removed. To determine the appropriate size of the femoral component, the surgeon reads the size indicia indicated by the highest exposed letter visible on the femoral sizer guide. For example, the set-up of FIG. 8 indicates that a size E femoral component is required for the femur. Next the surgeon determines the thickness of the tibial articulating surface (poly) required by reading the indicia 131 on the flexion poly thickness guide 130 aligned with a hash mark 41 formed on the face of the tensor 40. Referring again to FIG. 8, the set-up indicates that a 17 mm poly component is required for the patient's knee in flexion. As will be explained later, the reading from the flexion poly thickness guide is also used to determine an amount of distal femoral bone to be removed relative to a standard cut.

Figure 9:
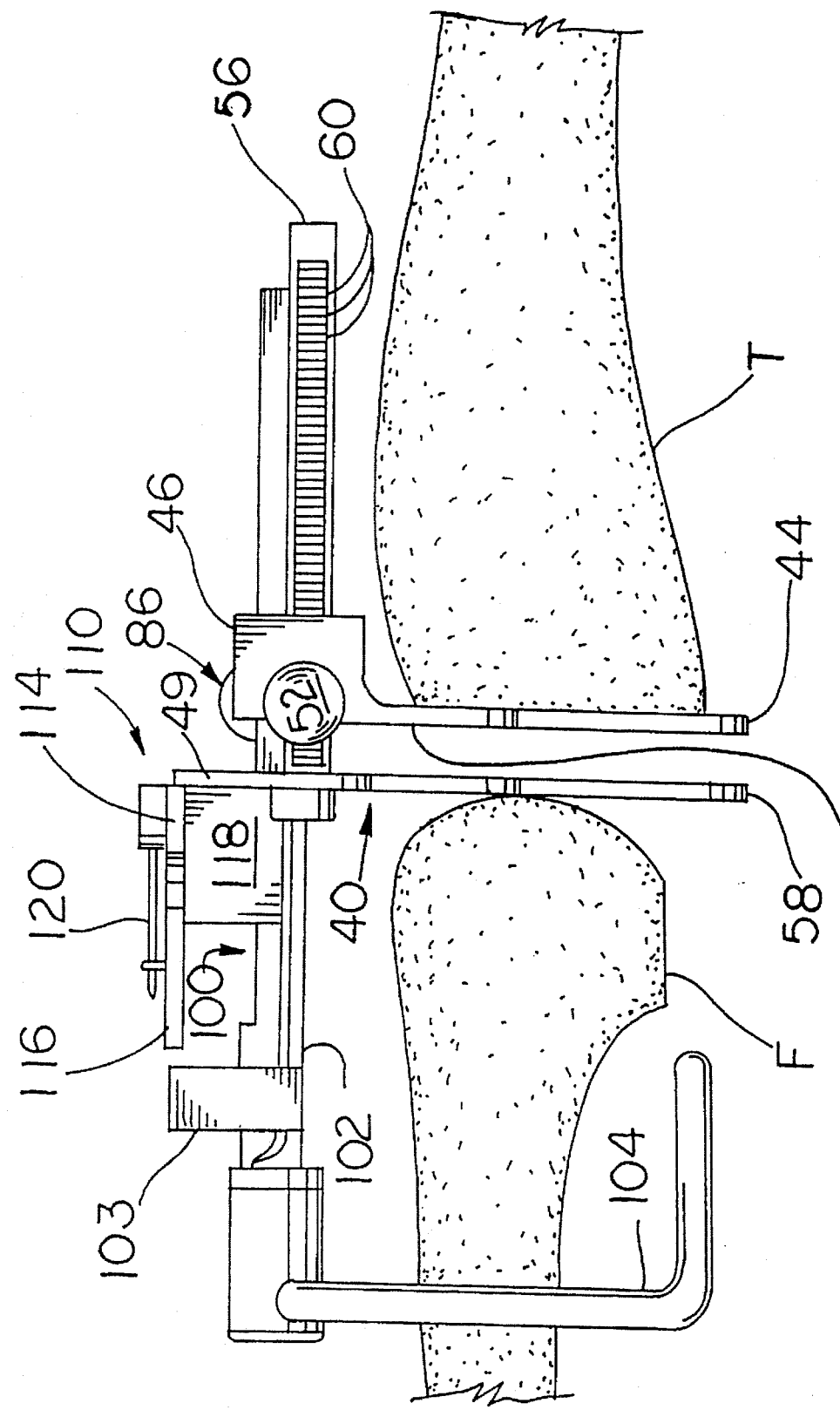
Figure 10:
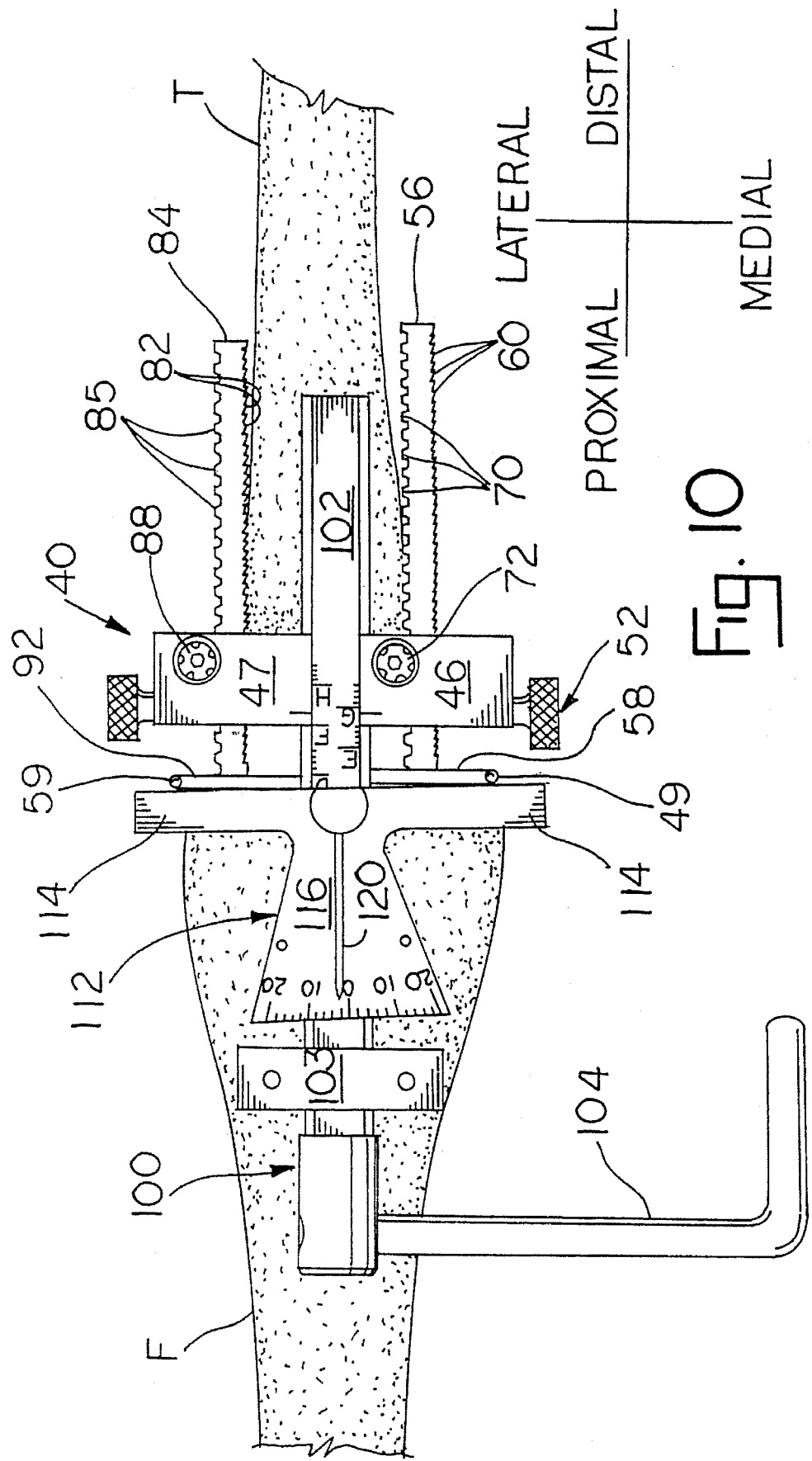
Figure 10A:
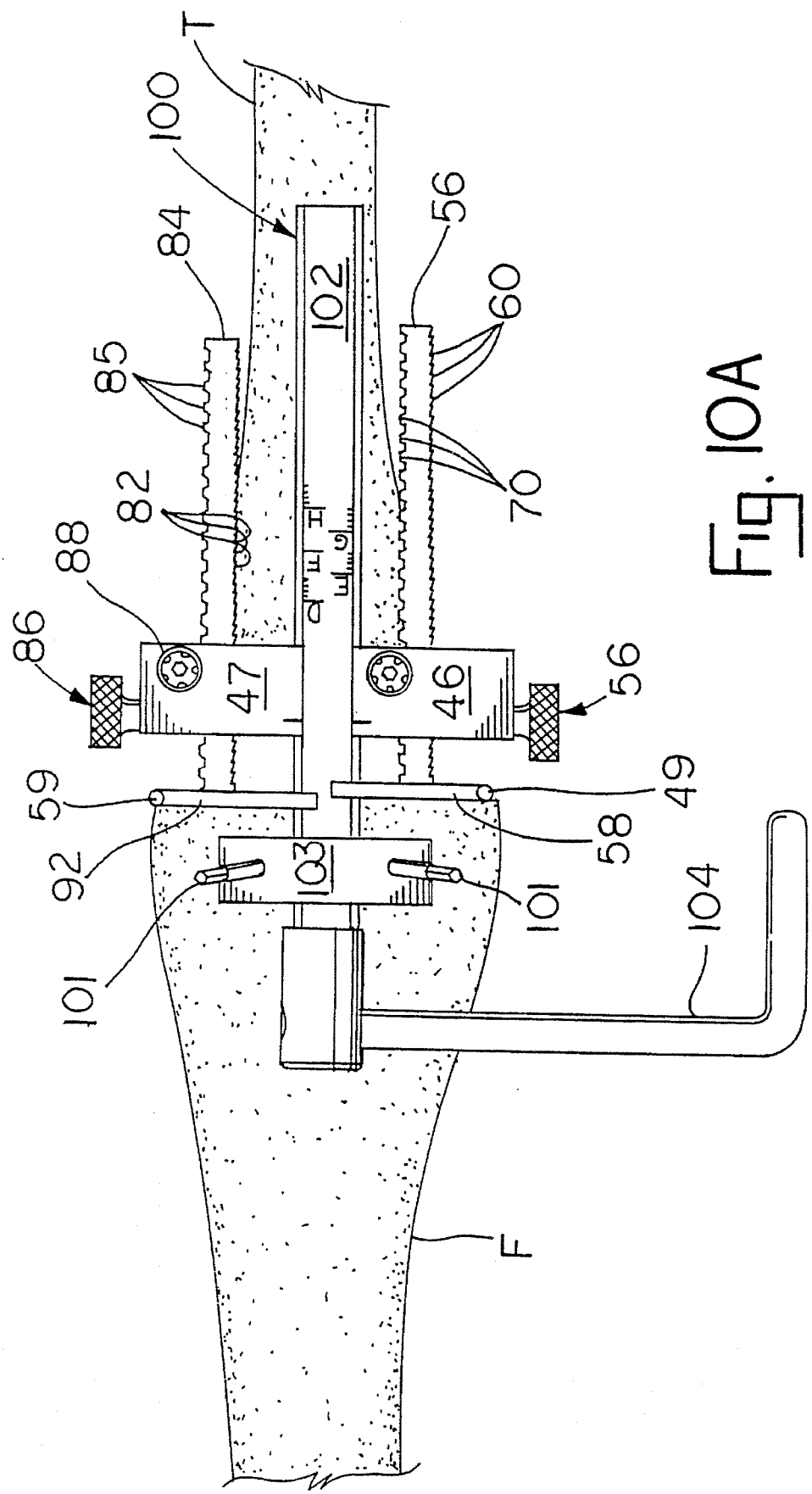

The surgeon then unlocks the tensor, places the knee in extension and again tenses the knee in a similar manner as was described above. With the knee in extension, the arm 104 of the sizer 100 is simply pivoted to a position adjacent the femur and out of the surgeon's way. An angular alignment indicator 110 is positioned on the femoral sizer 100 as illustrated in FIGS. 9 and 10 and is slid along the sizer shaft 102 until the legs 114 of body 112 of the indicator contacts the rods 49, 59 of the tensor paddles 58, 92. The indicator includes a C-shaped bracket 118 which fits onto shaft 102 of sizer 100. Bracket 118 is connected to a pointer needle 120. Needle 120 and bracket 118 are rotatable relative to body 112. As illustrated in FIG. 10, so positioned, the pointer or the indicator illustrates that the knee is currently set at approximately 3 degrees of angular offset. The angular alignment indicator 110 is used by the surgeon to ensure the joint is positioned or balanced at the appropriate amount of angular offset as determined preoperatively by the surgeon. This allows the surgeon to fine tune the soft tissue balance of the joint to allow the appropriate offset for the knee prosthesis. Once the surgeon is satisfied with the amount of angular offset, the angular alignment 110 indicator is removed and a pair of pins 101 are inserted into the openings of pinning guide 103 of the femoral sizer 100 (see FIG. 10A). Next the surgeon positions the extension poly thickness guide 140 in an overlying relationship to the femoral sizer 100 within slot 48 of tensor 40 as illustrated in FIG. 11. The extension poly thickness guide 140 includes a transverse arm 142 and is positioned similar to the flexion poly thickness guide described earlier. The extension poly thickness guide includes a plurality of indica 144. The surgeon reads indicia aligned with the hash mark 41 on the face of the tensioner 40. As illustrated in FIG. 12, the guide 140 indicates a number of 14.

The surgeon subtracts the reading from the extension poly thickness guide 130 from the reading obtained from the flexion poly thickness guide 140 to determine the amount of bone to be removed relative to a standard resection. Continuing the example illustrated in the figures, the reading in flexion was 17; subtract the reading in extension of 14;

leaves a remainder of 3. Therefore, the surgeon is told that for a proper soft tissue balance and ligament tension for the knee joint, an additional 3 mm of bone should be removed as compared to the standard cut. If the result would have been a negative number, the surgeon would adjust the instruments as explained below to resect 3 mm less relative to the standard cut.

Figure 13:
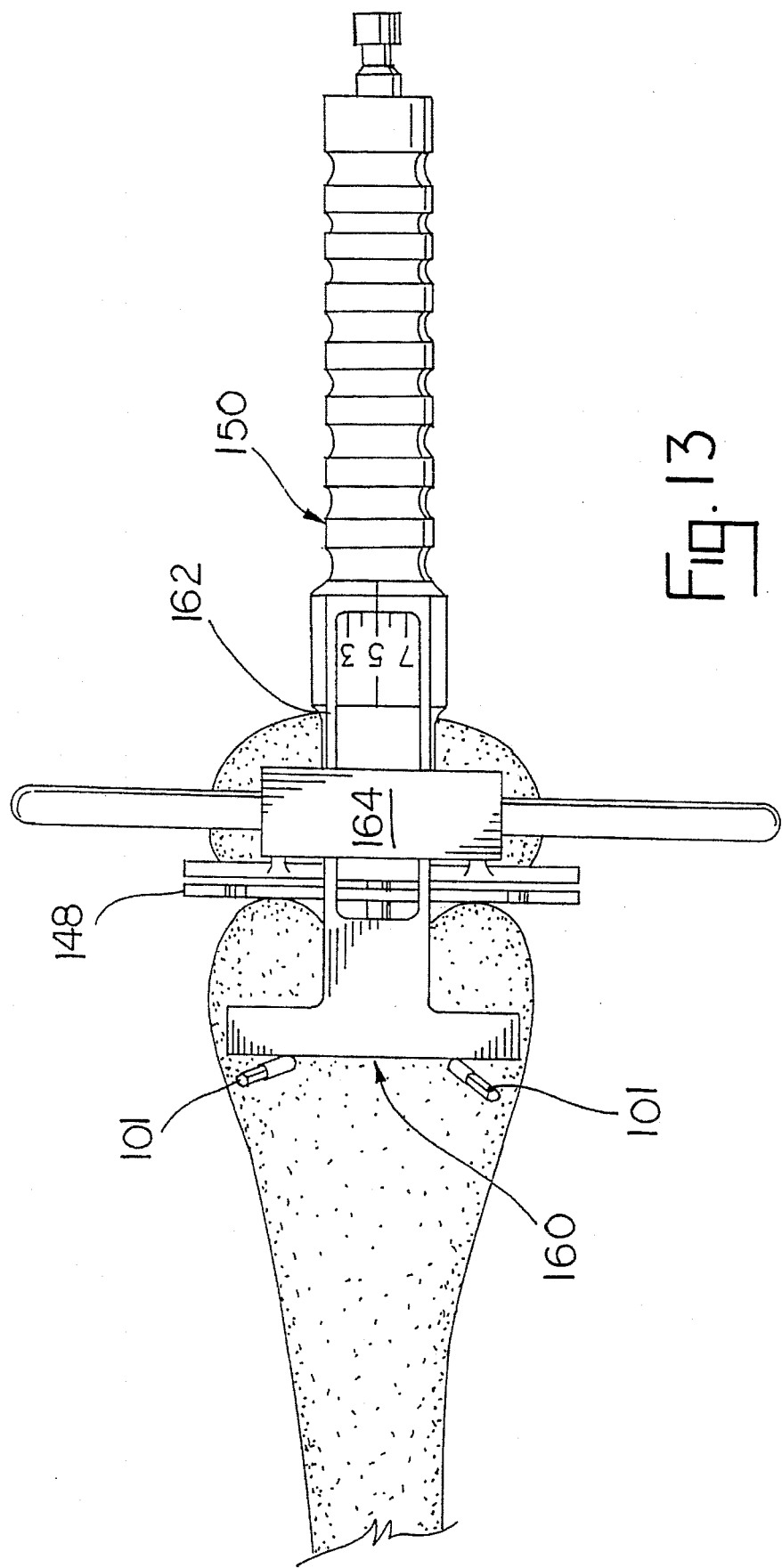

The surgeon selects a spacer plate 148 corresponding to the result obtained above and connects the plate to an intramedullary alignment guide 150 as illustrated in FIG. 13. The alignment guide as shown in FIG. 13 is more fully illustrated in co-pending U.S. patent application Ser. No. 08/265,884 filed on Jun. 17, 1994, and incorporated herein by reference. The alignment guide is adjusted in a manner explained in the incorporated application so that the angle of the spacer plate relative to the IM rod is set to the valgus angle preoperatively determined by the surgeon. The alignment guide includes a pair of slots through the spacer plate and base which the surgeon aligns with rotational reference marks formed in the femur in the step of FIG. 1. The surgeon may opt to insert a pair of pins in the reference marks to assist in aligning the guide. The alignment guide is inserted into the femur until the plate makes firm contact with the distal femur. As a final visual check for valgus alignment, the surgeon inserts a valgus alignment guide 160 onto the alignment guide 150 (see FIG. 13). The valgus alignment guide 160 includes a T-handle 162 slidably carried by body 164. The T-handle is slid toward the reference pins 101 placed in the femur as guided by the femoral sizer 100. If the head of the T-handle contacts both pins, the alignment guide 150 is set at the appropriate valgus angle to produce a rectangular joint space between the femur and tibia in extension. If one of the pins is not contacted, the surgeon has essentially four options; 1) accept the mismatch when it is very small; 2) adjust the valgus angle on the alignment guide until both pins are contacted; 3) adjust the soft tissues until both pins are contacted by the valgus alignment guide; or 4) re-cut the bone and realign the joint. The option chosen is dependant upon the size of the mismatch and surgeon preference. Once the surgeon is satisfied with the placement of the alignment guide, he removes the valgus alignment guide 160 and replaces it with bone milling instrumentation thereon as is fully illustrated and described in co-pending application Ser. No. 08/169,459 filed Dec. 17, 1993, and incorporated herein by reference.

The remainder of the description provides details on the design and function of each of the instruments discussed above.

Figure 14:
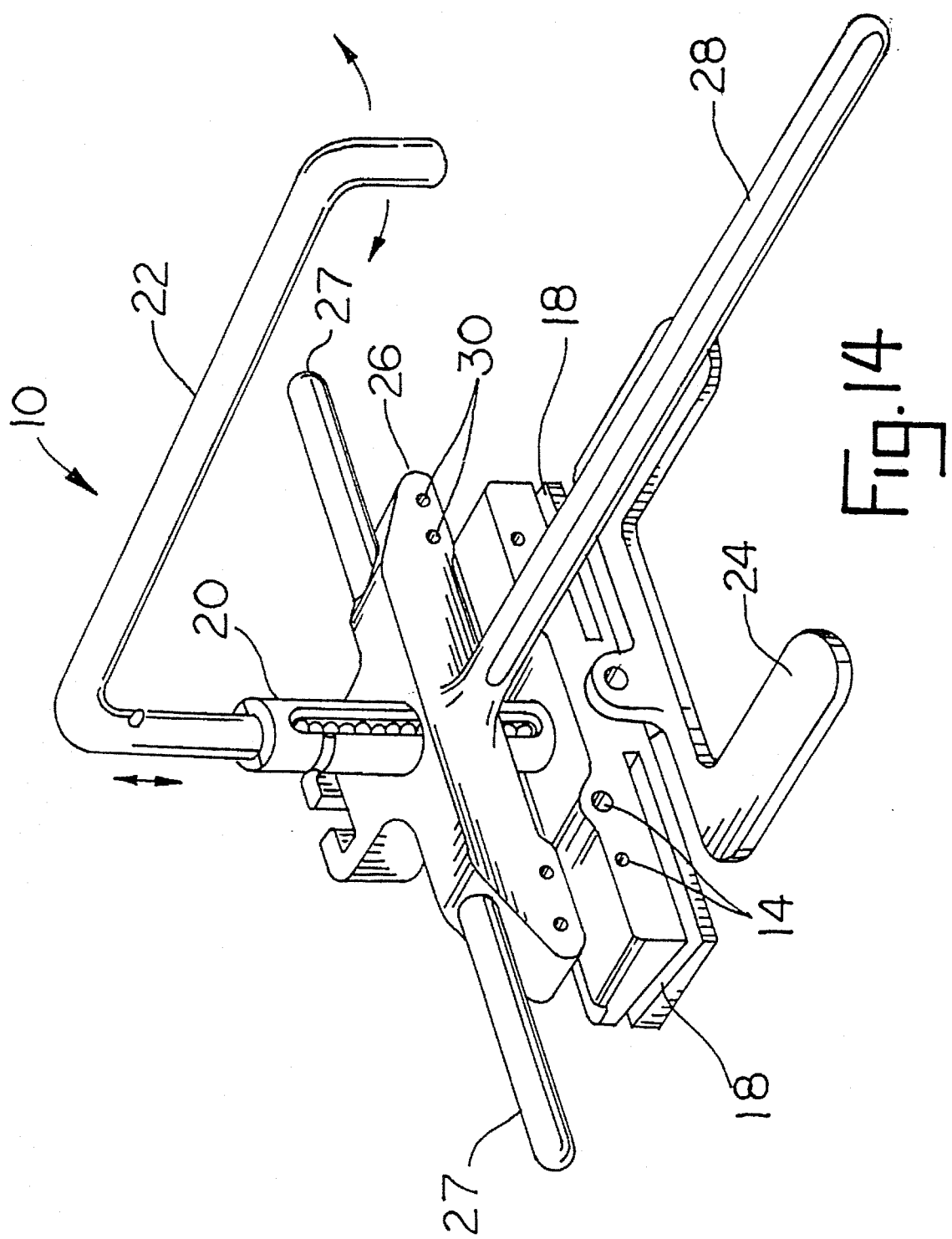
FIG. 14 is a perspective view of the rotational alignment guide of the invention.
Figure 15:
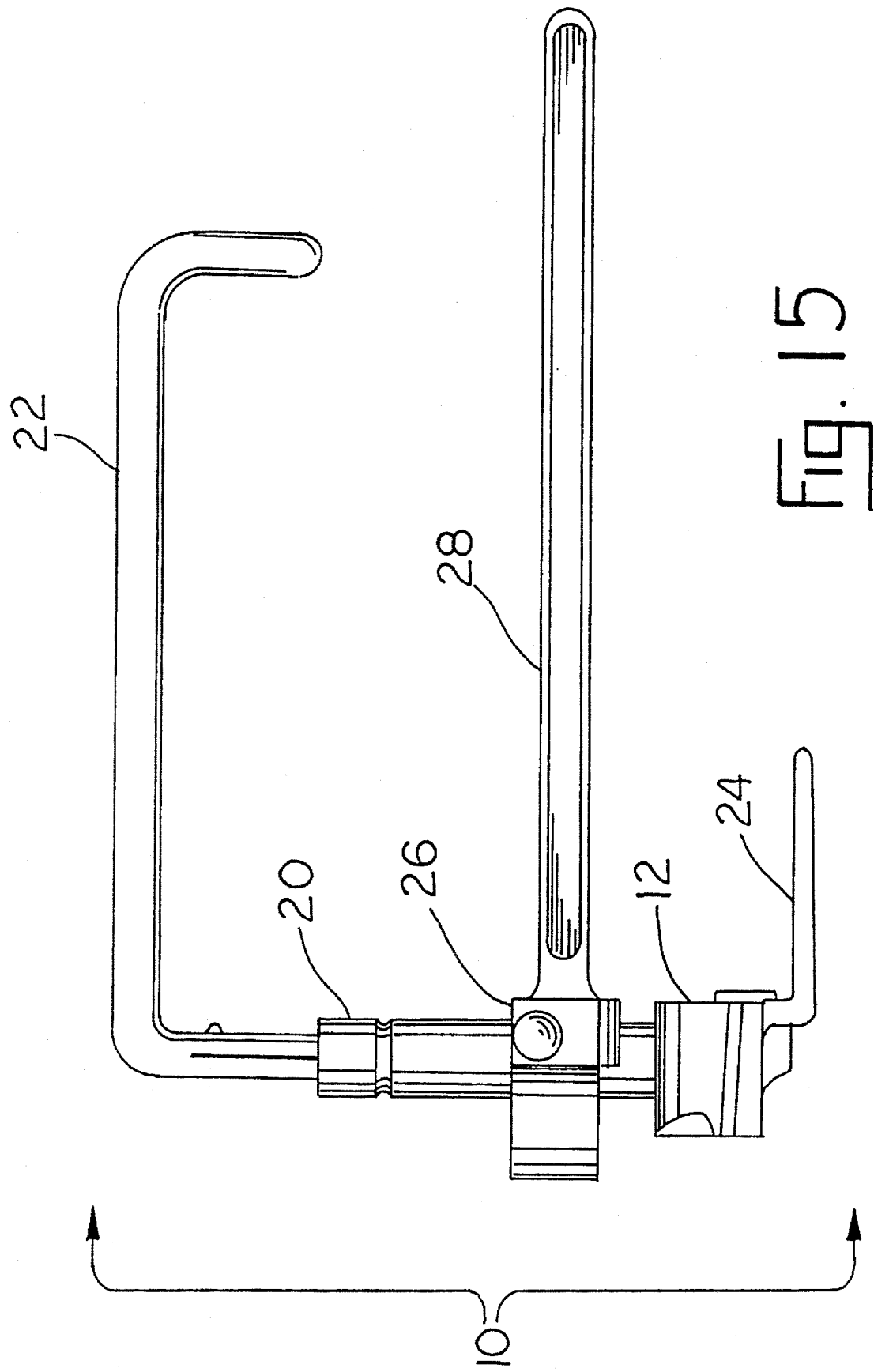
FIG. 15 is a side elevational view of the rotational alignment guide of FIG. 14.
Figure 16:
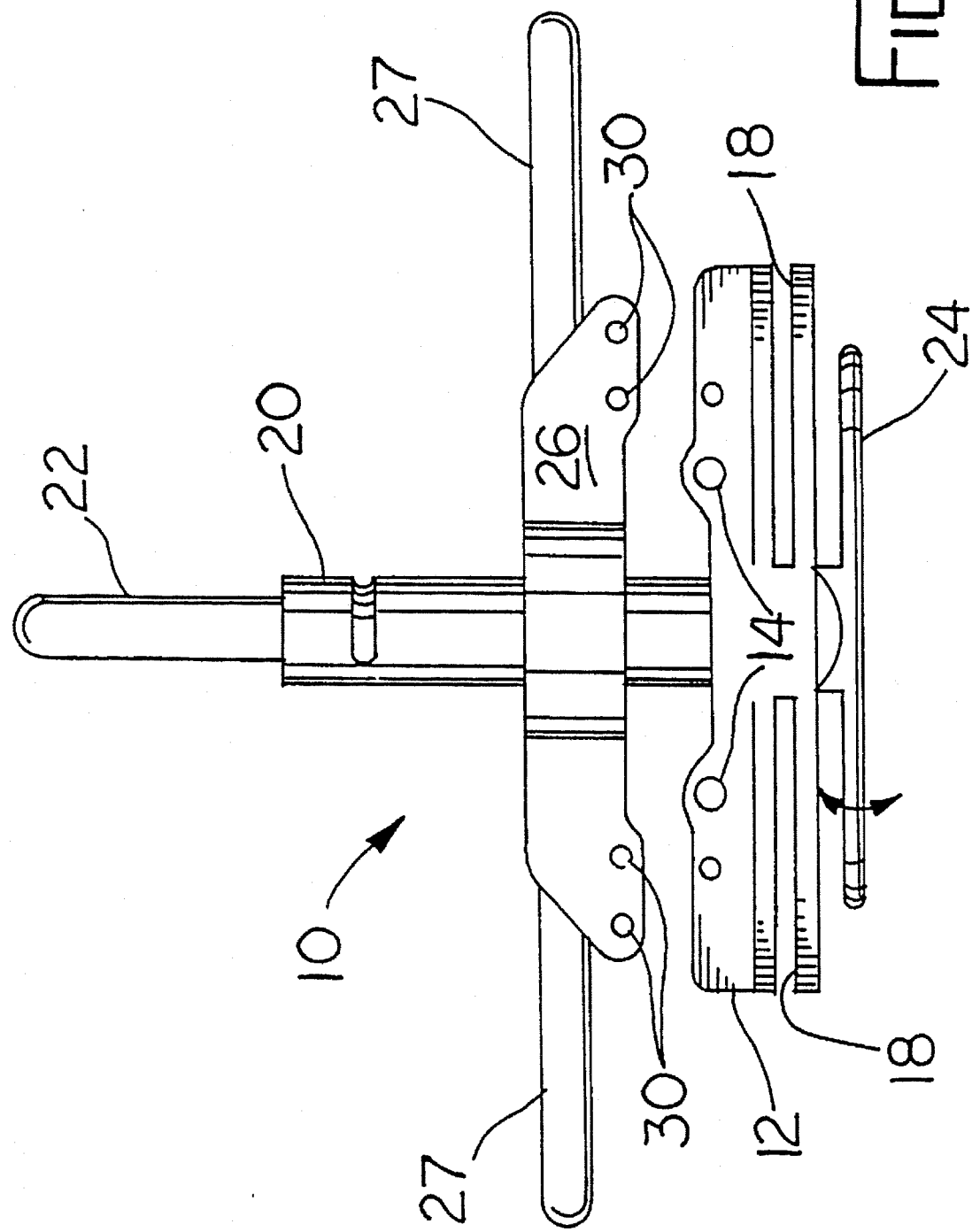
FIG. 16 is an end elevational view of the rotational alignment guide of FIG. 15 taken from line 16—16.

The rotational alignment guide 10 is illustrated in FIGS. 14 through 16 and includes a generally rectangular body 12 having a pair of opposed slots 18 extending therethrough as illustrated best in FIG. 16. Body 12 includes a plurality of bores 14 therethrough which accommodate pins for stabilizing the housing during resection of the posterior condyles. A tube 20 extends anteriorly from body 12 and includes a handle 22. A pair of reference feet 24 is connected to the body and extends proximally from the body. Reference feet 24 are removably attached to the body by a screw, for example (not shown). Reference feet 24 may be connected to the body such that they are allowed to pivot between predetermined angles. Alternatively, reference feet 24 may be formed so as to be set at a fixed angle relative to body 12. A pinning guide 26 is shiftably carried by tube 20 and extends substantially parallel to body 12. An intramedullary rod 28 extends proximally from pinning guide 26. As illustrated best in FIGS. 14 and 15, the pinning guide 26 includes a pair of bores 30 therethrough positioned on the medial and lateral sides of the pinning guide relative to tube 20. Arms 27 extend medially and laterally from pinning guide 26 and provide sighting means for the surgeon to visually align the guide 10 with known anatomical landmarks.

Figure 17:
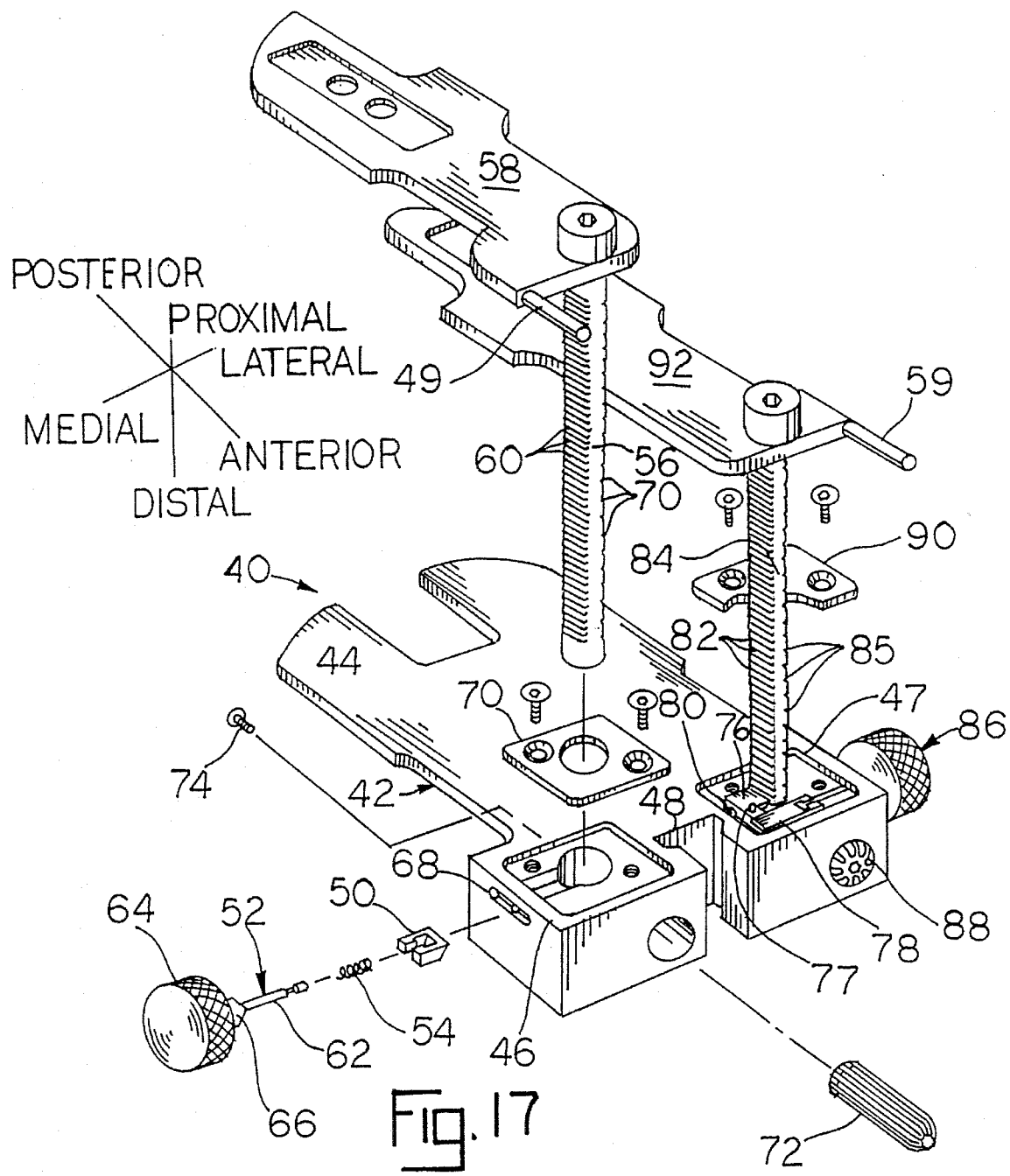
FIG. 17 is a perspective view of the tensor of the invention with portions exploded or sectioned for illustrative purposes.

Tensioner 40, illustrated in FIGS. 17 through 19, includes a housing 42 defining a first paddle 44 for contacting the tibia. Housing 42 further includes ratchet housings 46, 47, which are spaced apart by a T-shaped slot 48. Ratchet housing 46 carries a ratchet mechanism consisting of a pawl 50 and a release 52 connected to the pawl. A pawl spring 54, carried by the release mechanism and positioned between the ratchet housing and the pawl, biases the pawl into a ratchet engagement with ratchet teeth 60 on ratchet shaft 56 of paddle 58. As illustrated, ratchet shaft 56 is shiftably accommodated within an opening passing through ratchet housing 46 and includes ratchet teeth 60 along one longitudinal side of the shaft. Release 52 includes a shaft 62, which is rotatably connected to the pawl and a release knob 64. The inner surface of the release knob includes a pair of protrusions 66 (only one shown) spaced on opposite sides of the shaft. The protrusions are accommodated within a slot 68 of the ratchet housing 46. To release the pawl from the ratchet teeth and thereby allow the paddle 58 to shift toward paddle 44, the release knob is rotated, which causes protrusions 66 to be urged out of the slot 68 and into contact with the outer surface of the ratchet housing, thus shifting the release shaft and pawl medially until the pawl is spaced from the teeth. A rachet housing cover 70 is screwed onto the ratchet housing. Ratchet shaft 56 includes drive teeth 70 extending longitudinally along one side of the shaft generally opposite teeth 60. An elongated drive gear 72 is carried within an opening formed in ratchet housing 46 in engagement with drive teeth 70. A screw 74 secures drive gear 72 within the housing.

Ratchet housing 47 carries a pawl 76 which is pivotal within housing 47 about pivot pin 77. A pivot arm 78 is connected to the anterior end of pawl 76 and to the release shaft of release 86. A pawl spring 80 is positioned between the ratchet housing 47 and the lateral distal end of the pawl to urge the pawl into engagement with ratchet teeth 82 of ratchet shaft 84. Release 86 is substantially similar in construction and function to release 52 described above and need not be described further. As the release 86 is shifted laterally in response to contact between the protrusions and the housing 47, the pivot arm pulls on the anterior end of pawl 76 to pivot the posterior end out of engagement with the ratchet shaft 84. A drive gear 88 is carried by ratchet housing 47 and is held in rotational engagement by a screw (not shown). Ratchet shaft 84 includes drive teeth 85 which is engagable with drive gear 88. A ratchet cover 90 is connected to ratchet housing 47 by screws. A paddle 92 is connected to ratchet shaft 84. As illustrated, each paddle 58 and 92 includes a rod 49, 59 respectively, which extend in an anterior direction from the paddles. Rods 49, 59 are generally planar with their respective paddles and form reference surfaces for contact by the poly thickness gauges as described earlier. Drive gears 72 and 88 each include hexagonal openings formed therein for accommodating a tip of a torque driver. The torque driver tip is inserted into the drive gear opening and rotated in a clockwise direction to extend paddle 58 or 92 away from paddle 44. The ratchet mechanisms described prevents the paddles from shifting in the direction of paddle 44 until the release mechanisms are employed to disengage the pawls from the ratchet teeth.

Femoral sizer guide 100 (See FIGS. 20–22) includes a shaft 102 having a T-shaped cross section for slidable accommodation within the T-shaped slot 48 of tensor 40. A pinning guide 103 is connected to the shaft. Guide 100 further includes an arm 104 having a tip as illustrated. Arm 104 is rotationally connected to shaft 102. The anterior face of the shaft 102 includes a plurality of indicia thereon which correlates to the various sizes of femoral prosthetic components available to be implanted by the surgeon by the Assignee, Zimmer, Inc.

The angular alignment indicator 110 is illustrated in FIGS. 23–25 and includes a body 112 having a pair of opposed legs 114 and an indicator face 116. Face 116 includes indicia thereon which relates to the relative angle between the two paddles of the tensor relative to the shaft of the femoral sizing guide. Indicator 110 also includes a C-shaped bracket 118 which is connected through body 112 to an indicator needle 120. Bracket 118 and needle 120 are fixed relative to one another and are rotatable relative to the housing. In use, the bracket engages the femoral sizing guide 100 and the legs contact the rods 49 and 59 of the paddles.

It should be understood that the invention is not to be limited to the precise form disclosed but may be modified within the keeping of the following claims.

We claim:

1. In combination, a tensor device for use in a knee replacement surgery to exert tension between a distal femur and a proximal tibia of a knee joint and means connectable to the tensor for measuring a space between the distal femur and proximal tibia when the knee joint is positioned in extension and flexion, the tensor further includes a first paddle for contact with the proximal tibia and a second set of paddles for contact with the distal femur, the first paddle and second set of paddles including a gear drive means for separating the first paddle from the second set of paddles, ratchet means carried by the tensor engages the gear drive means to prevent the first paddle and second set of paddles from inadvertently shifting toward one another, and release means carried by the tensor for disengaging the ratchet means from the gear drive means to permit the first paddle and second set of paddles to shift toward one another wherein the release means includes a release shaft connected at one end to a pawl of the ratchet means and to a release knob at another end, the knob having at least one protrusion extending therefrom in the direction of the release shaft, the protrusion being accommodated within a slot of the tensor when the ratchet means is in engagement with the gear drive means, wherein as the release knob is rotated, the protrusion is drawn out of the slot and into contact with a side wall of the tensor to shift the ratchet means into disengagement with the gear drive means.

2. The combination of claim 1, wherein the measuring means includes a first sizer which slides onto the tensor when the knee joint is in flexion, the first sizer is adapted to contact an anterior distal portion of the femur, the first sizer includes first indicia thereon which relates to the size of a femoral component required for the distal femur.

3. The combination of claim 2, wherein the measuring means includes a second sizer which slides onto the tensor in a partial overlying relationship to the first sizer, the first sizer including a plurality of indicia thereon which relates to a plurality of prosthetic component sizes, the second sizer contacts the tensor in such a manner so that one of the indicia on said first sizer indicating a particular size of prosthetic component is aligned with an end of the second sizer.

4. The combination of claim 3 wherein the second sizer includes indicia thereon which relates to the space between the femur and the tibia.

5. The combination of claim 4 wherein said sizing means further includes a third sizer, which slides onto the tensor when the knee joint is in an extended position, the third sizer including indicia thereon which indicates the space between the femur and tibia when the knee joint is in extension.

6. In combination, a set of instruments for establishing and verifying a rotational alignment angle and a predetermined valgus angle for a knee joint during total knee arthroplasty and for assisting a surgeon in choosing the proper prosthetic components and ensuring a proper soft tissue balance for the knee joint prior to resection of the distal femur, the knee joint including a femur and tibia interconnected by soft tissue, the combination including;

an angular alignment guide, said angular alignment guide including means for establishing rotational alignment guide marks on the distal end of the femur, said guide marks relating to the preferred rotational angle for a knee joint;

a tensor apparatus for placement between the femur and tibia of the knee joint, said tensor apparatus including means for tensioning the soft tissues interconnecting the femur and tibia; and measurement means connectable to the tensor apparatus for indicating to a surgeon the proper size of prosthetic components compatible with the knee joint and for indicating to the surgeon the space between the tibia and femur, wherein said measurement means includes a femoral sizing guide which is slidably accommodated within the tensor and includes an arm adapted for contacting an anterior surface of the femur when the knee joint is positioned in flexion, the measurement means further including a flexion polymer thickness guide which is positioned in overlying relationship to the femoral sizing guide and includes indicia thereon relating to the size of the space between the femur and the tibia when the knee joint is positioned in flexion, wherein the measurement means further includes an extension polymer thickness guide which is carried by the tensor when the knee joint is positioned in extension and includes indicia thereon which relates to the size of the space between the femur and tibia when the knee joint is positioned in extension.

7. The combination of claim 6 wherein said angular alignment means includes a verification means for verifying the knee joint is positioned at an appropriate valgus angle as predetermined by the surgeon.

8. The combination of claim 6 further including a pinning guide for placement of a pair of alignment pins within the femur, said pinning guide being slidably carried by the tensor apparatus.

9. A method of establishing and verifying a rotational alignment angle and a predetermined valgus angle for a knee joint during total knee arthroplasty and for assisting a surgeon in choosing the proper prosthetic components and ensuring a proper soft tissue balance for the knee joint prior to resection of the distal femur, the knee joint including a femur and tibia interconnected by soft tissue, the method comprising the steps of:

a) surgically exposing a knee joint and placing the knee joint in a flexion position, the joint including a proximal tibia and a distal femur, the distal femur including posterior condyles;

b) providing a rotational alignment guide and inserting said rotational alignment guide into the femur and aligning the rotational alignment guide with known anatomical landmarks;

c) providing a saw blade and guiding said saw blade within slots formed in the rotational alignment guide for resecting the posterior condyles so that the surface formed is substantially parallel to the tibia;

d) providing a tensioner device and inserting said tensioner device between the tibia and femur and manipulating the tensioner device until a predetermined amount of force is applied to the tensioner device to separate the femur and the tibia;

e) providing a femoral sizing guide and placing said femoral sizing guide onto the tensioner device until a portion of the femoral sizing guide contacts the femur, the femoral sizing guide includes a plurality of indicia thereon for indicating the size of a femoral component required for the femur;

f) providing a flexion poly thickness guide and placing said flexion poly thickness guide onto the tensioner device, the flexion poly thickness guide including indicia thereon for indicating the size of a space between the femur and the tibia with the knee joint in flexion;

g) obtaining a reading from the femoral sizing guide;

h) obtaining a reading from the flexion poly thickness guide;

i) positioning the knee joint in an extended position, j) inserting the tensioner device between the tibia and femur and manipulating the tensioner device until a predetermined amount of force is applied to the tensioner device to separate the femur and the tibia;

k) providing an extension poly thickness guide and placing said extension poly thickness guide onto the tensioner device, the extension poly thickness guide including indicia thereon for indicating the size of a space between the femur and the tibia with the knee joint in extension;

l) obtaining a reading from the extension poly thickness guide; and m) subtracting the reading obtained from the extension poly thickness guide from the reading obtained from the flexion poly thickness guide to obtain a difference, wherein the difference indicates a variance to be factored into the amount of femur to be resected to accommodate a prosthetic component.

10. The method of claim 9 further including the steps of:

a) providing an angular alignment indicator and connecting said angular alignment indicator to the tensioner device when the knee joint is in the extended position for indicating an amount of angular offset for the knee joint, the angular alignment indicator including indicia thereon relating to the offset angle for the knee joint, said angular alignment indicator being connected to the tensioner device after step b.

11. The method of claim 9 wherein step e includes providing a pair of pins and inserting the pair of pins into the femur through pinning apertures formed on the femoral sizing guide after the femoral sizing guide contacts the femur.

12. The method of claim 11 wherein after said pair of pins are inserted into the femur the method further including the steps of;

a) providing an alignment guide and connecting said alignment guide to the distal femur, the alignment guide including a sliding handle member for contact with the pair of pins;

b) sliding the handle toward said pins until at least one pin is contacted by the handle.

* * * * *